(12) United States Patent
Gorlach

(10) Patent No.: US 9,573,990 B2
(45) Date of Patent: Feb. 21, 2017

(54) METHOD OF PRODUCING A PLURALITY OF ISOLATED ANTIBODIES TO A PLURALITY OF COGNATE ANTIGENS

(75) Inventor: Jorn Gorlach, Manchester, NJ (US)

(73) Assignee: MONTECITO BIO-SCIENCES, LTD., Montecito, CA (US)

( * ) Notice: Subject to any disclaimer, the term of this patent is extended or adjusted under 35 U.S.C. 154(b) by 721 days.

(21) Appl. No.: 13/253,366

(22) Filed: Oct. 5, 2011

(65) Prior Publication Data

US 2012/0029171 A1 Feb. 2, 2012

Related U.S. Application Data

(63) Continuation of application No. 11/221,252, filed on Sep. 7, 2005, now abandoned.

(60) Provisional application No. 60/608,526, filed on Sep. 9, 2004.

(51) Int. Cl.
*C07K 16/00* (2006.01)

(52) U.S. Cl.
CPC .................... *C07K 16/00* (2013.01)

(58) Field of Classification Search
CPC .................................................. C07K 16/00
USPC ..................................... 530/387.1; 435/69.6
See application file for complete search history.

(56) References Cited

U.S. PATENT DOCUMENTS 6,365,418 B1 4/2002 Wagner et al.
6,406,840 B1 6/2002 Li et al.

OTHER PUBLICATIONS

Babcock et al., "A novel strategy for generating monoclonal antibodies from single, isolated lymphocytes producing antibodies of defined specificities," Proc. Natl. Acad. Aci. 1996 93:7843-7848.
Weitkamp et al., "Generation of recombinant human monoclonal antibodies to rotavirus from single antigen-specific B cells seleted with fluorescent virus-like particles," Journal of Immunological Methods 2003 275:223-237.
De Wildt et al., "A new method for the analysis and production of monoclonal antibody fragments originating from single human B cells," Journal of Immunological Methods 1997 207:61-67.
Asano et al., "Efficient construction of a diabody using a refolding system: anti-carcinoembryonic antigen recombinant antibody fragment," J. Biochem 2002 132:903-909.

*Primary Examiner* — Lynn Bristol
(74) *Attorney, Agent, or Firm* — Licata & Tyrrell P.C.

(57) ABSTRACT

The present invention relates to a method for producing high affinity antibodies that are antigen-specific. The method involves binding a plurality of antibody-producing B-cells from a mammal to a plurality of cognate antigens; sorting the bound antibody-producing B-cell and cognate antigen; amplifying nucleic acid sequences encoding each antibody, or fragment thereof, from the B-cells; and expressing the each antibody in a protein expression system. Antibodies produced in this manner are useful in diagnostic and therapeutic applications.

1 Claim, 2 Drawing Sheets

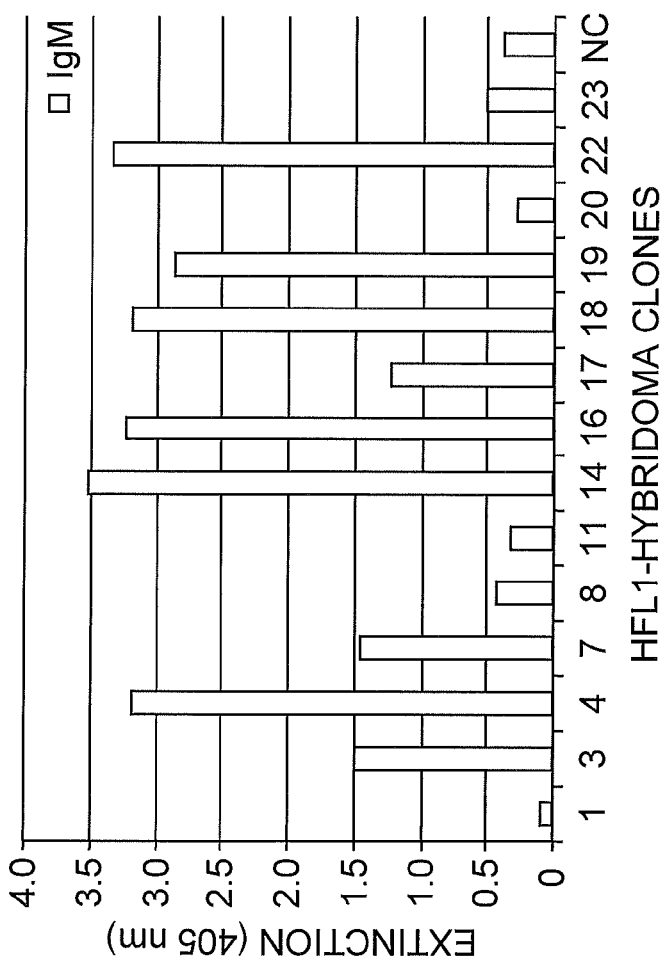
FIG. 2B
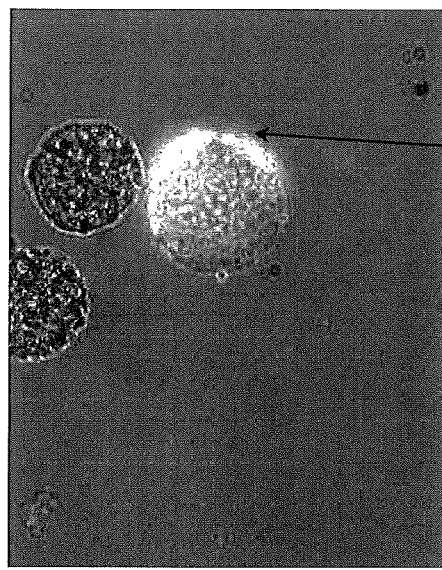
FIG. 2A
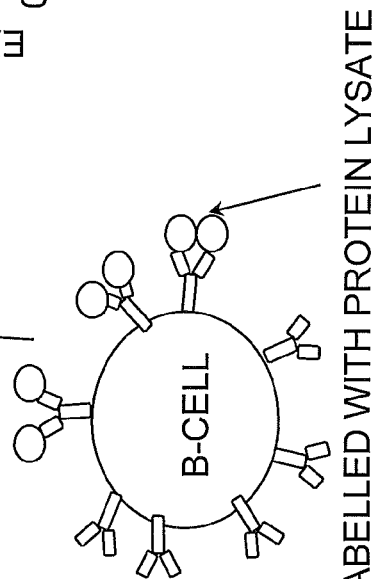

METHOD OF PRODUCING A PLURALITY OF ISOLATED ANTIBODIES TO A PLURALITY OF COGNATE ANTIGENS

INTRODUCTION

This application is a continuation of U.S. Ser. No. 11/221,252 filed Sep. 7, 2005, now abandoned claims the benefit of U.S. Provisional Application No. 60/608,526 filed Sep. 9, 2004, which are herein incorporated by reference in their entireties.

BACKGROUND OF THE INVENTION

Recent developments in antibody engineering and recombinant DNA technology have made it possible to generate recombinant antibodies with high specificity and affinity for theoretically any antigen by employing phage display technology and constructing very large repertoires of antibodies that are displayed on the surface of filamentous phage (Winter et. al., (1994) Ann. Rev. Immunol. 12:433-455). International patent application WO 92/18619 describes methods for producing a library of DNA molecules capable of expressing a fusion polypeptide on the surface of a filamentous phage particle (phagemids) and producing heterodimeric receptors such as antibodies, and T-cell receptors.

These large repertoires of naive, immunocompetent, or synthetic antibody fragments are fused to a minor phage coat protein; they are integrated into the DNA of the filamentous phage and displayed on the phage surface. Panning and selection of individual phage clones can screen the phage population containing tens of millions of individual clones through binding to an immobilized antigen (Barbas (1995) Nature Medicine 1:837-839). However, this is a very time-consuming process requiring as much as 6-10 weeks to complete, depending on the complexity of the antigen mixture.

After selection, antibody genes rescued from the phage genome can be expressed very efficiently in bacteria for the production of soluble, functional recombinant antibody fragments (Ward et. al., (1989) Nature 341:544-546). However, the disadvantage of such antibodies is that they are typically naive (i.e., non-immunocompetent) and therefore have a significantly lower binding affinity and are not as efficient or useful for binding experiments. Naïve antibodies are generally regarded as antibodies produced by B-cells that have not undergone class-switching and post-somatic hypermutation in response to exposure to antigen. In most animals, the initial exposure to an unknown antigen results in B-cell production of IgM class of antibodies of relatively low affinity. Subsequent exposure provides a selection process among B-cells whereby a genetic rearrangement occurs within the antibody gene of the corresponding B-cell. The result is a higher binding affinity antibody of a non-IgM class of immunoglobulin such as IgG, IgA, or IgE and their various species-specific subclasses. This in vivo response is critical for obtaining high quality antibodies with a high binding affinity and has yet to be routinely replicated in vitro.

Methods of producing a high affinity, monoclonal antibody to a specific antigen using single human B cells have been described (de Wildt, et al. (1997) J. Immunolog. Meth. 207:61-67; Weitkamp, et al. (2003) J. Immunolog. Meth. 275:223-237; Babcock, et al. (1996) Proc. Natl. Acad. Sci. USA 93:7843-7848). In general, these methods employ sorting methods to select for all antibody-secreting cells using a general cell-surface marker (e.g., CD19) or an enrichment step wherein B-cells are selected for binding to a specific antigen (e.g., U1A protein).

There is a need in the art for a high-throughput approach of producing antibodies with a high affinity and are antigen-specific. Moreover, it would be advantageous for these antibodies to be rapidly produced with minimal or no selection to eliminate the time-consuming processes of panning or screening. The present invention meets this need by providing a one-step selection process in combination with recombinant cell technologies.

SUMMARY OF THE INVENTION

The present invention is a method for producing a plurality of isolated antibodies to a plurality of cognate antigens. The method involves binding a plurality of antibody producing B-cells from a mammal to a plurality of cognate antigens; isolating each bound antibody producing B-cell and cognate antigen; amplifying nucleic acid sequences encoding each antibody, or fragment thereof, from the B-cells; introducing each nucleic acid sequence encoding each antibody, or fragment thereof, into an expression system capable of expressing an antibody so that a plurality of isolated antibodies to a plurality of cognate antigens is produced.

BRIEF DESCRIPTION OF THE DRAWINGS

FIG. 2A shows human lung protein lysate coupled to fluorescent beads, labeling the surface of a B-cell.

FIG. 2B shows the production of IgM antibodies by single, sorted B-cells after binding to cognate antigens from human lung fibroblasts.

DETAILED DESCRIPTION OF THE INVENTION

Figure 1:
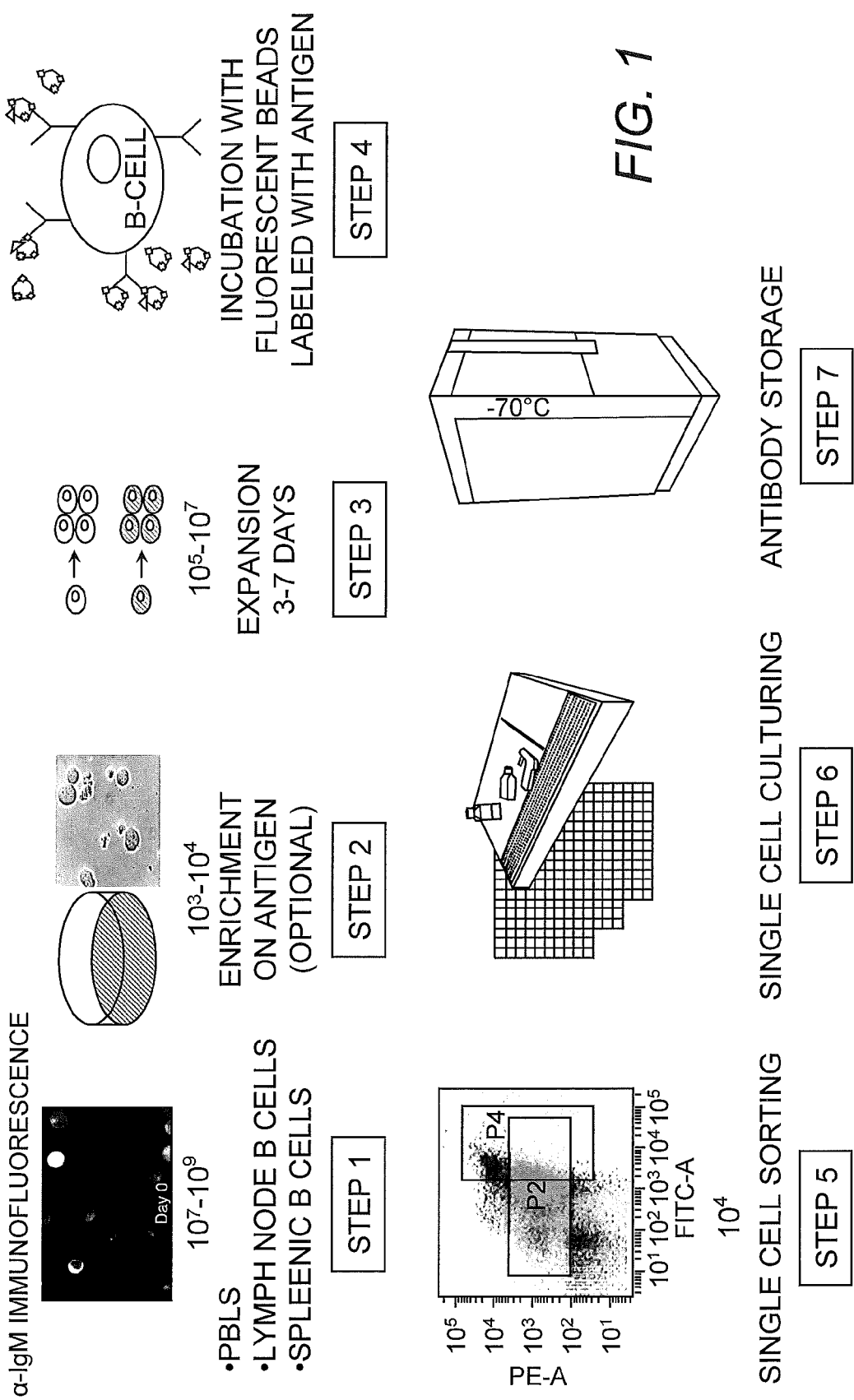
FIG. 1 is a schematic showing the steps of binding a plurality of antibody producing B-cells from a mammal to a plurality of cognate antigens and isolating each bound antibody producing B-cell and cognate antigen.

A high-throughput, one-step selection method for producing a plurality of antigen-specific antibodies has now been developed. The method of the invention is advantageous over the art in that a plurality or collection of antibodies can be produced in one step and said antibodies are antigen-specific, species-specific, and have a high affinity to their cognate antigens. The method of the invention involves binding a plurality of antibody-producing B-cells from a mammal to a plurality of cognate antigens; isolating each bound antibody-producing B-cell and cognate antigen; amplifying nucleic acid sequences encoding each antibody, or fragment thereof, from the B-cells; introducing each nucleic acid sequence encoding each antibody, or fragment thereof, into an expression system for expressing an antibody to produce a plurality of isolated antibodies to a plurality of cognate antigens. While recombinant technology is desirable, conventional hybridoma technology can also be employed.

As used herein, a plurality or collection of antibodies, antibody producing B-cells, or antigens is intended to be more than one distinct antibody or antigen, desirably between about 5 and 1000, more suitably between about 100 and 10,000. In particular embodiments, a plurality or collection is between about 1000 and 100,000. A collection can be more than 100,000 or more than one million.

Each B-cell produced by the body contains nucleic acid sequences encoding for one antibody which binds specifically to at least one epitope (i.e., binding partners). For use in the method of the present invention, the plurality of antibody-producing B-cells can be obtained from any appropriate source including peripheral blood lymphocytes, lymph node, bone marrow or spleen of mammalian origin using well-known isolation methods (e.g., gradient centrifugation for the isolation of peripheral blood lymphocytes). Mammals of particular interest include humans; laboratory animals such as mice, rats, or rabbits; farm animals such as goats, sheep, chickens, donkeys, cows and the like; pets such as cats or dogs; or other animal species. Further, a plurality of antibody-producing cells can be obtained from immortalized B-cells (e.g., immortalized by EBV or chemical agents) or from peripheral blood lymphocytes or spleens of animals specifically immunized with a particular antigen or plurality of antigens.

The plurality of antibody-producing B-cells can be directly sorted into single B-cells by binding to cognate antigens, or as an optional prestep, the B-cells can be enriched on the antigen and expanded (FIG. 1, steps 2 and 3). Enrichment is carried out by e.g., incubating the isolated B-cells with fluorescent labeled cell- or tissue-lysates prior to single cell sorting or by incubation of cell- or tissue-lysates immobilized on a culture dish. Further, the B-cells can be expanded for 3-7 days by incubating the cells under suitable cell culture conditions (e.g., RPMI1640 medium, 10% fetal calf serum at 37° C., 5% CO2).

The step of isolating each bound antibody producing B-cell and cognate antigen includes contacting the plurality of antibody-producing B-cells and plurality of antigens for a sufficient period of time for binding to occur between an antibody of a B-cell to a cognate antigen. The source of antigen can be the same species as that used to obtain the antibody-producing B-cells or can be from a different or related species. Further, the plurality of antigens can be obtained from an organism (e.g., a virus, bacterium, fungus, or protozoan) which elicits an immune response to generate antibody-producing B-cells which specifically bind antigens of said organism. A plurality of antigens can be of one macromolecular species; e.g., only proteins, peptides, glycoproteins, carbohydrates, lipids, or nucleic acids; or can be a mix of macromolecular species. Moreover, the plurality of antigens can contain intracellular, extracellular, and/or secreted macromolecules of known or unknown identity or function. A plurality of antigens can be an extract from a whole sample (e.g., a cellular complex, organelle, cell, tissue, organ, bodily fluid or whole organism) or a fraction of the sample (e.g., cellular fractionation using liquid-phase fractionation techniques such as chromatography (Labrou (2003) J. Chromatogr. B Analyt. Technol. Biomed. Life Sci. 790(1-2):67-78); hydrophobic, hydrophilic, isoelectric focusing; ligand binding; or size separation). A plurality of antigens can be related macromolecules. The different antigens can be either functionally related or just suspected of being functionally related. The antigens can share a similarity in structure or sequence or are simply suspected of sharing a similarity in structure or sequence. For instance, a plurality of antigens can be all growth factor receptors, hormone receptors, neurotransmitter receptors, catecholamine receptors, amino acid derivative receptors, cytokine receptors, extracellular matrix receptors, lectins, cytokines, serpins, proteases, kinases, or polypeptides isolated from a specific cell, organ or tissue type. A plurality of antigens can also be from a specific disease, physiological or developmental state. As used herein, disease or disease state or condition refers to any perturbation of the normal state that results in a change in epitope expression patterns or localization. Examples of perturbations include, but are not limited to, exposure to an allergen; immunological disorders; neoplasms; malignancies; metabolic disorders; all organ and tissue disorders, such as of the heart, liver, prostate, lung, pancreas, skin, eye, nervous system, lymphatic system, colon and breast; aging; dementia; mental disorders; therapeutic drug treatment; and medical interventions, such as grafts, transplants, drug disorders, pathogen attack, or drought or saline growth conditions (e.g., in plants).

The step of isolating each bound antibody-producing B-cell and cognate antigen can be carried out in a number of ways. In one embodiment, individual antigens or individual B-cells of a plurality of antigens or a plurality of B-cells, respectively, are placed in a well or spot on a membrane (i.e., in an array), contacted with a plurality of the respective binding partner, washed to remove non-specific binding interactions so that individual antibodies and their cognate antigens remain bound. When either the plurality of antigens or plurality of B-cells are separated on an array prior to contact with the cognate binding partner, the step of isolating the bound antibody and antigen from the plurality occurs simultaneously with the binding step.

Methods of arraying macromolecules or B-cells are well-known in the art. Typically, arrays comprise micrometer-scale, two-dimensional patterns of patches of antigens or B-ells immobilized on an organic thin-film coating on the surface of the substrate. Examples of arrayed antigen or cell chips, including array pattern and density, substrates, coatings and organic thin-films are described in the art, for example, WO 02/14866; U.S. Pat. Nos. 6,329,209; 6,365,418; and 6,406,840, each of which are incorporated by reference in their entirety.

An array of antigens or B-cells comprises a substrate, at least one organic thin-film covering some or all of the surface of the substrate, and a plurality of patches arranged in discrete, known regions on the portions of the substrate surface covered by organic thin-film, wherein each patch contains antigens or cells immobilized on the organic thin-film, wherein said antigens or cells of a given patch are bind a particular binding partner in a plurality of binding partners, and the array contains a plurality of antigens or B-cells, desirably between about 10 and 10,000, each of which binds a cognate binding partner in a plurality of binding partners.

The antigens or B-cells are generally covalently immobilized on the patches of the array, either directly or indirectly, for example, glutaraldehyde can be used to immobilize a protein and collagen can be used to immobilize a cell.

In general, only one type of antigen or one B-cell is present on a single patch of the array. If more than one type of antigen or B-cell is present on a single patch, all of the antigens or B-cells of that patch must share a common binding partner (i.e. cell or antigen, respectively). For example, a patch can contain a variety of antibodies to the same polypeptide although, potentially, the antibodies can bind different epitopes on that same polypeptide.

Optimal binding is achieved by contacting a plurality of antigens or B-cells on an array with a plurality of cognate binding partners in a suitable container, under a cover slip, etc, or incorporation into a structure that provides for ease of analysis, high throughput, or other advantages, such as in a biochip format, a multiwell format and the like. For example, the subject arrays could be incorporated into a biochip type device. A biochip type device is, e.g., a substantially rectangular shaped cartridge containing fluid entry and exit ports and a space bounded on the top and bottom by substantially planar rectangular surfaces, wherein the array is present on one of the top and bottom surfaces. Such a device is disclosed in U.S. Pat. No. 6,287,768 and is incorporated herein by reference in its entirety.

Alternatively, the subject arrays could be incorporated into a high throughput or multiwell device, wherein each array is bound by raised walls in a manner sufficient to form a reaction container wherein the array is the bottom surface of the container.

Contact of an array and a plurality of binding partners involves contacting the array with an aqueous medium containing the binding partners. Contact can be achieved in a variety of different ways depending on specific configuration of the array. For example, where the array is incorporated into a biochip device having fluid entry and exit ports, the probe solution can be introduced into the chamber in which the pattern of target molecules is presented through the entry port, where fluid introduction could be performed manually or with an automated device. In multiwell embodiments, the probe solution will be introduced in the reaction chamber containing the array, either manually, e.g., with a pipette, or with an automated fluid handling device. Alternatively, the array can be subjected to centrifugal force to overcome non-specific binding forces that limit the rate of liquid flow, thus allowing for an increase in agitation and related replenishment rates. Such an apparatus used to facilitate array hybridization is disclosed in U.S. Pat. No. 6,309,875, which is incorporated herein by reference in its entirety.

In an alternative embodiment, the plurality of B-cells or plurality of antigens are bound prior to the isolation step by adding the plurality of B-cells to a point of application, such as a tube or a well in a plate containing the plurality of antigens so that individual antibody-producing B-cells and their cognate antigens bind. Subsequently, the bound B-cells and cognate antigens are sorted from other bound and non-bound members of the collections (FIG. 1, steps 4 and 5). In this embodiment, the step of isolating or sorting is generally carried out using cell-sorting methods such as fluorescence-activated cell sorting (FACS), hydraulic or laser capture microdissection in combination with laser confocal microscopy or fluorescence microscopy, changes in mass or by using a continuous flow apparatus wherein the bound binding partners are channeled into individual wells. While no label can be used in the step of sorting bound binding agents and epitopes, typically, either one or both (i.e., applying Fluorescence Resonance Energy Transfer (FRET) or bioluminescence resonance energy transfer (BRET) techniques) binding partners are labeled, suitably with a fluorescent or bioluminescent tag, and upon binding are detected and isolated based on the binding interaction. Fluorochromes such as Phycocyanine, Allophycocyanine, Tricolor, AMCA, Eosin, Erythrosin, Fluorescein, Fluorescein Isothiocyanate Hydroxycoumarin, Rhodamine, Texas Red, Lucifer Yellow, and the like can be attached directly to one or both binding partners through standard groups such as sulfhydryl or primary amine groups. Those of ordinary skill in the art will know of other suitable labels which can be employed in accordance with the present invention. The binding of these labels to antibodies can be accomplished using standard techniques (see, for example, Kennedy, et al. (1976) Clin. Chim. Acta 70:1-31 and Schurs, et al. (1977) Clin. Chim Acta 81:1-40). Subsequent to sorting, the isolated B-cells can be cultured and stored for further use (FIG. 1, steps 6 and 7).

Using the binding and sorting steps of the present invention, single, sorted B-cells were isolated which produced IgM antibodies specific for human lung proteins (FIG. 2).

In contrast to other methods of producing monoclonal antibodies wherein the B-cells are immortalized by hybridoma or EBV methods, an antibody produced by the method of the present invention is maintained or cloned by amplifying nucleic acid sequences encoding each antibody, or fragment thereof, from the bound and isolated B-cells and introducing or cloning said sequences into an expression system.

As used herein, an antibody, or fragment there of, can be a member of any immunoglobulin class, including any of the human classes: IgG, IgM, IgA, IgD, and IgE. However, an antibody, or fragment of an IgG class is desirable in the present invention. Antibody fragments can be any derivative of an antibody which is less than full-length. Generally, an antibody fragment retains at least a significant portion of the full-length antibody's specific binding ability. Examples of antibody fragments include, but are not limited to, Fab, Fab', F(ab')2, scFv, Fv, dsFv, diabody, Fd fragments or microbodies, for example, U.S. patent application No. 20020012909. An antibody can also include bispecific and chimeric antibodies.

Using species-specific oligonucleotides which hybridize to sequences flanking nucleic acid sequences encoding the antibody genes, methods such as single-cell reverse transcriptase PCR (Coronella, et al. (2000) Nucleic Acids Res. 28(20):E85) are used to amplify variable heavy and light chain nucleic acid sequences or fragments thereof. For example, human variable heavy and light chain antibody domains can be PCR-amplified using human-specific oligonucleotides (see, e.g., Sblattero and Bradbury (1998) Immunotechnology 3:271-278). Amplified sequences can be characterized by DNA sequencing, directly cloned as individual sequences into an expression system, or operably linked so that the heavy and light chain nucleic acid sequences are expressed as one contiguous, in-frame protein. Using such methods as gene splicing by overlap extension (i.e. SOE-PCR; Horton, et al. (1989) Gene 77(1):61-8) hybrid heavy and light chain nucleic acid sequences can be generated.

Subsequently, the amplified nucleic acid sequences are introduced into any suitable expression system for storage and future use. Methods for producing recombinant proteins such as antibodies in expression systems are well-known in the art. In general, nucleic acid sequences encoding the antibody, or fragment thereof, are incorporated into a recombinant expression vector in a form suitable for expression of the antibody, or fragment thereof, in a host cell. A suitable form for expression provides that the recombinant expression vector includes one or more regulatory sequences operatively-linked to the nucleic acids encoding the antibody, or fragment thereof, in a manner which allows for transcription of the nucleic acids into mRNA and translation of the mRNA into the protein. Regulatory sequences may include promoters, enhancers and other expression control elements (e.g., polyadenylation signals). Such regulatory sequences are known to those skilled in the art and are described in Goeddel D. D., ed., Gene Expression Technology, Academic Press, San Diego, Calif. (1991). It should be understood that the design of the expression vector may depend on such factors as the choice of the host cell to be transfected and/or the level of expression required.

An antibody, or fragment thereof, can be expressed not only directly, but also as a fusion protein with a heterologous polypeptide, i.e. a signal sequence for secretion and/or other polypeptide which will aid in the purification of the antibody, or fragment thereof. Desirably, the heterologous polypeptide has a specific cleavage site to remove the heterologous polypeptide from the antibody, or fragment thereof.

In general, a signal sequence can be a component of the vector and should be one that is recognized and processed (i.e., cleaved by a signal peptidase) by the host cell. For production in a prokaryote, a prokaryotic signal sequence from, for example, alkaline phosphatase, penicillinase, lpp, or heat-stable enterotoxin II leaders may be used. For yeast secretion, one may use, e.g., the yeast invertase, alpha factor, acid phosphatase leaders, the Candida albicans glucoamylase leader (EP 362,179), or the like (see, for example WO 90/13646). In mammalian cell expression, signal sequences from secreted polypeptides of the same or related species, as well as viral secretory leaders, for example, the herpes simplex glycoprotein D signal may be used.

Other useful heterologous polypeptides which can be fused to an antibody, or fragment thereof, include those which increase expression or solubility, aid in the purification, or label (e.g., GFP) the antibody. Typical fusion expression vectors include fusion vectors of c-Myc, HA, or myc/his6 (e.g., pHen1) as well as pGEX vectors (Amersham Biosciences, Piscataway, N.J.), and pMAL and pTYB vectors (New England Biolabs, Beverly, Mass.) which fuse glutathione-S-transferase or maltose E binding protein, or an intein/chitin binding domain, respectively, to the target recombinant antibody.

An antibody, or fragment thereof, is expressed in a cell by introducing nucleic acid sequences encoding the antibody, or fragment thereof, into a host cell, wherein the nucleic acids are in a form suitable for expression of the antibody, or fragment thereof, in the host cell. Alternatively, nucleic acid sequences encoding the antibody, or fragment thereof, which are operatively-linked to regulatory sequences (e.g., promoter sequences) but without additional vector sequences can be introduced into a host cell. As used herein, a host cell is intended to include any prokaryotic or eukaryotic cell or cell line so long as the cell or cell line is not incompatible with the protein to be expressed, the selection system chosen or the fermentation system employed.

Eukaryotic cell or cell lines which can be used to produce an antibody, or fragment thereof, include mammalian cell lines as well as non-mammalian cells. Exemplary mammalian cell lines include, but are not limited to, CHO dhfr-cells (Urlaub and Chasin (1980) Proc. Natl. Acad. Sci. USA 77:4216-4220), 293 cells (Graham, et al. (1977) J. Gen. Virol. 36:59) or myeloma cells like SP2 or NSO (Galfre and Milstein (1981) Meth. Enzymol. 73(B):3-46). A variety of non-mammalian eukaryotic cells may be used as well, including insect (e.g,. *Spodoptera frugiperda*), yeast (e.g., *S. cerevisiae, Schizosaccharomyces pombe, Pichia pastoris, Kluveromyces lactic, Hansenula polymorpha*, and *Candida albicans*), fungal cells (e.g., *Neurospora crassa, Aspergillus nidulins, Aspergillus fumigatus*) and plant cells.

While any prokaryotic cell can be used to produce an antibody, or fragment thereof, *Escherichia coli* is the most common prokaryotic expression system. Strains which may be used to maintain expression plasmids include, but are not limited to, JM103, JM105, and JM107. Exemplary *E. coli* strains for protein production include W3110 (ATCC 27325), *E. coli* B, *E. coli* X1776 (ATCC 31537), *E. coli* BL21 (Amersham Biosciences, Piscataway, N.J.), *E. coli* ER5266 (New England Biolabs, Beverly, Mass.) and *E. coli* 294 (ATCC 31446).

For production of an antibody, or fragment thereof, in recombinant prokaryotic expression vectors it is contemplated that protein expression can be regulated by promoters such as the beta-lactamase (penicillinase) and lactose promoter systems (Chang, et al. (1978) Nature 275:615; Goeddel, et al. (1979) Nature 281:544), a tryptophan (trp) promoter system (Goeddel, et al. (1980) Nucl. Acids Res. 8:4057; EP 36,776) the tac promoter (De Boer, et al. (1983) Proc. Natl. Acad. Sci. USA 80:21) or pL of bacteriophage 1. These promoters and Shine-Dalgarno sequence can be used for efficient expression of an antibody, or fragment thereof, in prokaryotes. *E. coli* display systems have also been described (Kjaergaard, et al. (2002) J. Bacteriol. 184(15): 4197-204; Alcala, et al. (2003) FEBS Lett. 533(1-3):115-8).

Eukaryotic microbes such as yeast can be transformed with suitable vectors containing nucleic acids encoding an antibody, or fragment thereof. *Saccharomyces cerevisiae* is the most commonly studied lower eukaryotic host microorganism, although a number of other species already mentioned are commonly available. Yeast vectors can contain an origin of replication from the 2 micron yeast plasmid or an autonomously replicating sequence (ARS), a promoter, nucleic acid sequences encoding an antibody, or fragment thereof, sequences for polyadenylation and transcription termination, and nucleic acid sequences encoding a selectable marker. Exemplary plasmids include YRp7 (Stinchcomb, et al. (1979) Nature 282:39; Kingsman, et al. (1979) Gene 7:141; Tschemper, et al. (1980) Gene 10:157), pYepSec1 (Baldari, et al. (1987) Embo J. 6:229-234), pMFa (Kurjan and Herskowitz (1982) Cell 30:933-943), pJRY88 (Schultz, et al. (1987) Gene 54:113-123), and pYES2 (Invitrogen™ Corporation, San Diego, Calif.). These plasmids contain genes such as trp1, which provides a selectable marker for a mutant strain of yeast lacking the ability to grow in the presence of tryptophan, for example ATCC No. 44076 or PEP4-1 (Jones (1977) Genetics 85:12). The presence of the trp1 lesion in the yeast host cell genome then provides an effective environment for detecting transformation by growth in the absence of tryptophan.

Suitable sequences for promoting antibody expression in yeast vectors include the promoters for metallothionein, 3-phosphoglycerate kinase (Hitzeman, et al. (1980) J. Biol. Chem. 255:2073) or other glycolytic enzymes (Hess, et al. (1968) J. Adv. Enzyme Reg. 7:149; Holland, et al. (1978) Biochemistry 17:4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further disclosed in EP 73,657.

Further, an antibody of the invention can be expressed on the surface of a yeast cell (i.e., yeast display; Feldhaus, et al. (2003) Nat. Biotechnol. 21(2):163-70).

When the host cell is from an insect (e.g., *Spodoptera frugiperda* cells), expression vectors such as the baculovirus expression vector (e.g., vectors derived from *Autographa californica* MNPV, *Trichoplusia ni* MNPV, *Rachiplusia ou* MNPV, or *Galleria ou* MNPV, as described in U.S. Pat. Nos. 4,745,051 and 4,879,236) may be employed to express an antibody, or fragment thereof. In general, a baculovirus expression vector contains a baculovirus genome containing nucleic acid sequences encoding an antibody inserted into the polyhedrin gene at a position ranging from the polyhedrin transcriptional start signal to the ATG start site and under the transcriptional control of a baculovirus polyhedrin promoter.

In plant cells, expression systems are often derived from recombinant Ti and Ri plasmid vector systems. In the cointegrate class of shuttle vectors, the gene of interest is inserted by genetic recombination into a non-oncogenic Ti plasmid that contains both the cis-acting and trans-acting elements required for plant transformation. Exemplary vectors include the pMLJ1 huttle vector (DeBlock, et al. (1984) EMBO J. 3:1681-1689) and the non-oncogenic Ti plasmid pGV2850 (Zambryski, et al. (1983) EMBO J. 2:2143-2150). In the binary system, the gene of interest is inserted into a shuttle vector containing the cis-acting elements required for plant transformation. The other necessary functions are provided in trans by the non-oncogenic Ti plasmid. Exemplary vectors include the pBIN19 shuttle vector (Bevan (1984) Nucl. Acids Res. 12:8711-8721) and the non-oncogenic Ti plasmid pAL4404 (Hoekema, et al. (1983) Nature 303:179-180) and derivatives thereof.

Promoters used in plant expression systems are typically derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV).

In mammalian cells the recombinant expression vector can be a plasmid. Alternatively, a recombinant expression vector can be a virus, or a portion thereof, which allows for expression of a nucleic acid introduced into the viral nucleic acid. For example, replication-defective retroviruses, adenoviruses and adeno-associated viruses can be used. Protocols for producing recombinant retroviruses and for infecting cells in vitro or in vivo with such viruses can be found in Current Protocols in Molecular Biology, Ausubel, F. M. et al. (eds.) John Wiley & Sons, (1996), Section 9 and other standard laboratory manuals. Examples of suitable retroviruses include, but are not limited to, pLJ, pZIP, pWE and pEM which are well-known to those skilled in the art. Examples of suitable packaging virus lines include, but are not limited to, ψCrip, ψCre, ψ2 and ψAm. The genome of adenovirus can be manipulated such that it encodes and expresses an antibody but is inactivated in terms of its ability to replicate in a normal lytic viral life cycle (Berkner, et al. (1988) BioTechniques 6:616; Rosenfeld, et al. (1991) Science 252:431-434; Rosenfeld, et al. (1992) Cell 68:143-155). Suitable adenoviral vectors derived from the adenovirus strain Ad type 5 dl324 or other strains of adenovirus (e.g., Ad2, Ad3, Ad7 etc.) are well-known to those skilled in the art. Alternatively, an adeno-associated virus vector such as that taught by Tratschin, et al. ((1985) Mol. Cell. Biol. 5:3251-3260) may be used to express an antibody, or fragment thereof.

In mammalian expression systems, the regulatory sequences are often provided by the viral genome. Commonly used promoters are derived from polyoma, Adenovirus 2, cytomegalovirus and Simian Virus 40. For example, the human cytomegalovirus IE promoter (Boshart, et al. (1985) Cell 41:521-530), HSV-Tk promoter (McKnight, et al. (1984) Cell 37:253-262) and β-actin promoter (Ng, et al. (1985) Mol. Cell. Biol. 5:2720-2732) may be useful in the expression of an antibody in mammalian cells. Alternatively, the regulatory sequences of the recombinant expression vector can direct expression of an antibody preferentially in a particular cell-type, i.e., tissue-specific regulatory elements can be used. Examples of tissue-specific promoters which can be used include, but are not limited to, the albumin promoter (liver-specific; Pinkert, et al. (1987) Genes Dev. 1:268-277), lymphoid-specific promoters (Calame and Eaton (1988) Adv. Immunol. 43:235-275), promoters of T cell receptors (Winoto and Baltimore (1989) EMBO J. 8:729-733) and immunoglobulins (Banerji, et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci USA 86:5473-5477), pancreas-specific promoters (Edlund, et al. (1985) Science 230:912-916), and mammary gland-specific promoters (e.g., milk whey promoter; U.S. Pat. No. 4,873,316; EP 264,166). Developmentally-regulated promoters are also encompassed, for example the murine hox promoters (Kessel and Gruss (1990) Science 249:374-379) and the α-fetoprotein promoter (Camper and Tilghman (1989) Genes Dev. 3:537-546).

Nucleic acid sequences or expression vectors harboring nucleic acid sequences encoding an antibody may be introduced into a host cell by standard techniques for transforming cells. Transformation or transfection are intended to encompass all conventional techniques for introducing nucleic acid into host cells, including calcium phosphate co-precipitation, DEAE-dextran-mediated transfection, lipofection, electroporation, microinjection, polyethylene glycol-mediated transformation, viral infection, Agrobacterium-mediated transformation, cell fusion, and ballistic bombardment. Suitable methods for transforming host cells may be found in Sambrook, et al. (Molecular Cloning: A Laboratory Manual, 3rd Edition, Cold Spring Harbor Laboratory Press (2000)) and other laboratory manuals.

The number of host cells transformed with a nucleic acid sequence encoding an antibody, or fragment thereof, will depend, at least in part, upon the type of recombinant expression vector used and the type of transformation technique used. Nucleic acids can be introduced into a host cell transiently, or more typically, for long-term expression of an antibody, or fragment thereof, the nucleic acid sequence is stably integrated into the genome of the host cell or remains as a stable episome in the host cell. Plasmid vectors introduced into mammalian cells are typically integrated into host cell DNA at only a low frequency. In order to identify these integrants, a gene that contains a selectable marker (e.g., drug resistance) is generally introduced into the host cells along with the nucleic acids of interest. Preferred selectable markers include those which confer resistance to certain drugs, such as G418 and hygromycin. Selectable markers may be introduced on a separate plasmid from the nucleic acids of interest or introduced on the same plasmid. Host cells transfected with nucleic acid sequences encoding an antibody, or fragment thereof, (e.g., a recombinant expression vector) and a gene for a selectable marker may be identified by selecting for cells using the selectable marker. For example, if the selectable marker encodes a gene conferring neomycin resistance, host cells which have taken up the nucleic acid sequences of interest can be selected with G418 resistance. Cells that have incorporated the selectable marker gene will survive, while the other cells die.

A host cell transformed with nucleic acid sequences encoding an antibody, or fragment thereof, can be used for expressing an antibody, or fragment thereof, for protein production or can be used in cell-based screening assays.

Nucleic acid sequences encoding an antibody, or fragment thereof, can be introduced into cells growing in culture in vitro by conventional transformation techniques (e.g., calcium phosphate precipitation, DEAE-dextran transfection, electroporation, etc.). Nucleic acids can also be transferred into cells in vivo, for example by application of a delivery mechanism suitable for introduction of nucleic acid into cells in vivo, such as retroviral vectors (see, e.g., Ferry, et al. (1991) Proc. Natl. Acad. Sci. USA 88:8377-8381; Kay, et al. (1992) Hum. Gene Ther. 3:641-647), adenoviral vectors (see e.g., Rosenfeld (1992) Cell 68:143-155; Herz and Gerard (1993) Proc. Natl. Acad. Sci. USA 90:2812-2816), receptormediated DNA uptake (see e.g., Wu and Wu (1988) J. Biol. Chem. 263:14621; Wilson, et al. (1992) J. Biol. Chem. 267:963-967; U.S. Pat. No. 5,166,320), direct injection of DNA uptake (see e.g., Acsadi, et al. (1991) Nature 334:815-818; Wolff, et al. (1990) Science 247:1465-1468) or particle bombardment (see e.g., Cheng, et al. (1993) Proc. Natl. Acad. Sci. USA 90:4455-4459; Zelenin, et al. (1993) FEBS Let. 315:29-32).

Nucleic acid sequences encoding an antibody, or fragment thereof, can be transferred into a fertilized oocyte of a non-human animal to create a transgenic animal which expresses the antibody, or fragment thereof, in one or more cell-types. A transgenic animal is an animal having cells that contain a transgene, wherein the transgene was introduced into the animal or an ancestor of the animal at a prenatal, e.g., an embryonic, stage. A transgene is a DNA which is integrated into the genome of a cell from which a transgenic animal develops and which remains in the genome of the mature animal, thereby directing the expression of an encoded gene product in one or more cell-types or tissues of the transgenic animal. Exemplary examples of non-human animals include, but are not limited to, mice, goats, sheep, pigs, cows or other domestic farm animals. Such transgenic animals are useful, for example, for large-scale production of an antibody, or fragment thereof, (e.g., gene pharming) or for basic research investigations.

A transgenic animal can be created, for example, by introducing a nucleic acid sequence encoding an antibody, or fragment thereof, typically linked to appropriate regulatory sequences, such as a constitutive or tissue-specific enhancer, into the male pronuclei of a fertilized oocyte, e.g., by microinjection, and allowing the oocyte to develop in a pseudopregnant female foster animal. Intron sequences and polyadenylation signals may also be included in the transgene to increase the efficiency of expression of the transgene. Methods for generating transgenic animals, particularly animals such as mice, have become conventional in the art and are described, for example, in U.S. Pat. Nos. 4,736,866 and 4,870,009. A transgenic founder animal may be used to breed additional animals carrying the transgene.

Once produced, an antibody, or fragment thereof, can be recovered from culture medium or milk as a secreted polypeptide, although it also can be recovered from host cell lysates when directly expressed without a secretory signal. When an antibody, or fragment thereof, is expressed in a recombinant cell other than one of human origin, the antibody, or fragment thereof, is free of proteins or polypeptides of human origin. However, it may be necessary to purify the antibody, or fragment thereof, from recombinant cell proteins or polypeptides to obtain preparations that are substantially homogeneous as to the antibody, or fragment thereof. As a first step, the culture medium or lysate is centrifuged to remove particulate cell debris. The membrane and soluble protein fractions are then separated. The antibody, or fragment thereof, may then be purified from the soluble protein fraction. The antibody, or fragment thereof, thereafter is purified from contaminant soluble proteins and polypeptides with, for example, the following suitable purification procedures: by fractionation on affinity or ion-exchange columns; ethanol precipitation; chitin column chromatography, reverse-phase HPLC; chromatography on silica or on a cation-exchange resin such as DEAF; chromatofocusing; SDS-PAGE; ammonium sulfate precipitation; gel filtration using, for example, SEPHADEX G-75; ligand affinity chromatography, Ni-NTA column chromatography and protein A SEPHAROSE columns.

Antibodies identified by the method of the invention can be used individually or as a plurality of antibodies (i.e., as an antibody repertoire) in drug design, drug targeting, basic research, or diagnostic applications.

For example, arrays of antibodies can be used to profile antigens derived from patient tissue samples at various intervals of drug treatment to identify antigens that are regulated by said drug treatment. Furthermore, regulation of antigen expression by drug candidates can be evaluated with model systems to determine drug toxicity and efficacy. For example, using an array of antibodies, profiles of antigen expression can be generated for samples treated with known therapeutic agents or known toxins. This can be accomplished with cell lines in vitro or in various model systems, depending on the disease state being investigated. These profiles are then compared to antigen expression profiles of samples treated with unknown agents or toxins. As more profiles are generated, more definitive information concerning unknown agents or toxins is elucidated. In addition, these same profiles can be compared against patient profiles to monitor efficacy and toxicity of therapeutic drug treatment. This can provide valuable information at all stages of clinical drug trials as well as subsequent monitoring of patients undergoing drug treatment.

Furthermore, an array of antibodies can be used in a clinical or hospital setting to identify patients that can have an adverse reaction to a specific drug or class of drugs or that might react in a very positive manner to a certain therapeutic drug treatment. A patient tissue sample would be taken and analyzed by the appropriate array of antibodies to produce a disease biomarker profile. The profile can be generated at one time point or over multiple time points. These profiles are then compared to a vast database of profiles from other patients, treatments, model systems, and possibly even a previous profile from the same patient to identify any biomarkers associated with disease, toxicity, or therapeutic enhancement.

As one skilled in the art can appreciate, an array of antibodies has a plurality of uses. Such uses include, but are not limited to, identification of cell-to-cell and molecular interactions, drug mode-of-action studies, cellular localization studies, investigation of molecular pathways, baseline determinations, drug toxicity studies, drug interaction studies, chemical inhibition analyses, metabolic profiling and the like.

Antibodies of the present invention can also be used in the treatment of a disease state. In providing a patient with an antibody, or fragments thereof, the antibody, or fragment thereof, is used in an amount effective to substantially alter or reduce, e.g., reduce by at least about 50%, the disease state or symptoms in the recipient.

To achieve the desired reductions, an antibody, or fragments thereof, can be administered in a variety of unit dosage forms. The dose will vary according to the particular antibody. For example, different antibodies, or fragments thereof, can have different masses and/or affinities, and thus require different dosage levels.

Administration of an antibody, or fragments thereof, will generally be performed by an intravascular route, e.g., via intravenous infusion by injection. Other routes of administration can be used if desired. Formulations suitable for injection are found in Remington: The Science and Practice of Pharmacy, Alfonso R. Gennaro, editor, 20th ed. Lippincott Williams & Wilkins: Philadelphia, Pa., 2000. Such formulations must be sterile and non-pyrogenic, and generally will include a pharmaceutically effective carrier, such as saline, buffered (e.g., phosphate buffered) saline, Hank's solution, Ringer's solution, dextrose/saline, glucose solutions, and the like. The formulations may contain pharmaceutically acceptable auxiliary substances as required, such as, tonicity adjusting agents, wetting agents, bactericidal agents, preservatives, stabilizers, and the like.

An antibody identified by the method of the present invention also can be used as delivery vehicles for drugs. For example, a cytotoxic drug may be covalently or noncovalently associated with an antibody, or fragment thereof, whose binding partner is a cell surface polypeptide only expressed in cells involved in the development of a disease state. The cytotoxic drug-antibody combination would provide specific delivery of the cytotoxic drug to the cell of interest and minimize side effects associated with the delivery of said drug to other cell types.

An antibody identified by the method of the present invention can also be used as an imaging marker. For example, a commonly used radiochemical such as Technicium can be covalently or noncovalently associated with a an antibody whose binding partner is a cell surface polypeptide only expressed in cells involved in the development of a disease state. The radiochemical-antibody combination would provide for the clinical imaging, visualization and therefore detection of a disease state without the administration of large amounts of non-specific radiochemical and non-specific results. In this case only the disease state, such as a tumor, would be identified with a high level of confidence of the diagnosis.

What is claimed is:

1. A method for producing a plurality of isolated antibodies for profiling antigen expression comprising
    (a) binding, in vitro, an isolated plurality of antibody-producing B-cells to an isolated plurality of cognate antigens from a mammal;
    (b) isolating each cognate antigen-bound antibody-producing B-cell;
    (c) amplifying each nucleic acid sequence encoding each antibody, or fragment thereof, from each B-cell;
    (d) introducing each amplified nucleic acid sequence encoding each antibody, or fragment thereof, into an expression system;
    (e) expressing and purifying each antibody, or fragment thereof; and
    (f) preparing an array consisting of each purified antibody, or fragment thereof, from step (e) on a substrate for profiling antigen expression.

* * * * *